United States Patent
Dalko et al.

(10) Patent No.: US 9,381,143 B2
(45) Date of Patent: Jul. 5, 2016

(54) USE OF SUBSTITUTED METHOXYALKOXYPHENYLALKYL DERIVATIVES AS PRESERVATIVE, PRESERVING METHOD, COMPOUNDS AND COMPOSITION

(75) Inventors: Maria Dalko, Versailles (FR); Laurent Gilbert, Fourqueux (FR)

(73) Assignee: L'OREAL, Paris (FR)

( * ) Notice: Subject to any disclaimer, the term of this patent is extended or adjusted under 35 U.S.C. 154(b) by 243 days.

(21) Appl. No.: 13/824,172

(22) PCT Filed: Oct. 6, 2011

(86) PCT No.: PCT/EP2011/067450
§ 371 (c)(1),
(2), (4) Date: May 22, 2013

(87) PCT Pub. No.: WO2012/045809
PCT Pub. Date: Apr. 12, 2012

(65) Prior Publication Data
US 2013/0230473 A1    Sep. 5, 2013

Related U.S. Application Data

(60) Provisional application No. 61/392,082, filed on Oct. 12, 2010.

(30) Foreign Application Priority Data

Oct. 8, 2010  (FR) ..................... 10 58182

(51) Int. Cl.
| | | |
|---|---|---|
| A61K 8/02 | (2006.01) | |
| A61K 8/35 | (2006.01) | |
| A61K 8/34 | (2006.01) | |
| A61K 9/00 | (2006.01) | |
| A61K 47/08 | (2006.01) | |
| A61Q 19/00 | (2006.01) | |
| C07C 43/23 | (2006.01) | |
| C07C 49/255 | (2006.01) | |
| A61Q 5/00 | (2006.01) | |
| A61Q 17/04 | (2006.01) | |
| A61Q 19/04 | (2006.01) | |

(52) U.S. Cl.
CPC ... *A61K 8/35* (2013.01); *A61K 8/34* (2013.01); *A61K 8/347* (2013.01); *A61K 9/0014* (2013.01); *A61K 47/08* (2013.01); *A61Q 5/00* (2013.01); *A61Q 17/04* (2013.01); *A61Q 19/00* (2013.01); *A61Q 19/002* (2013.01); *A61Q 19/04* (2013.01); *C07C 43/23* (2013.01); *C07C 49/255* (2013.01); *A61K 2800/524* (2013.01)

(58) Field of Classification Search
None
See application file for complete search history.

(56) References Cited

U.S. PATENT DOCUMENTS

| 2,700,041 A | 1/1955 | Weston et al. | |
|---|---|---|---|
| 2010/0278991 A1* | 11/2010 | Haught et al. | 426/532 |

FOREIGN PATENT DOCUMENTS

| EP | 0316790 A1 | 5/1989 |
|---|---|---|
| EP | 1510511 A1 | 3/2005 |
| KR | 2002043072 A | 6/2002 |
| WO | WO-2004/014416 A1 | 2/2004 |
| WO | WO-2008/126057 A2 | 10/2008 |

OTHER PUBLICATIONS

Takagaki et al., Topical Application of Ethyl Ether to Recurrent Herpes Simplex, Apr. 1981, The Journal of Dermatology, vol. 8, Issue 2, pp. 109-111, Abstract.*
Junkichi Murai, Synthesis of m-hydroxyphenylethyl methyl ketone and 3-hydroxy-4-methoxyphenylethyl ketone (isozingerone), Science Reports of the Tohoku Imerial, Volumn 14, Series 1, pp. 149-154, 1925.*
XP002633833—Database WPI Week 200279 Thomson Scientific, Longdon, GB; AN 2002-729659, Oct. 5, 2011.
XP009133328—Mannich et al., "Über einige vom 1-Phenyl-3-amino-butan sich ableitende Phenolbasen", Archiv Der Pharmazie, Wiley-VCH Verlag Gmbh & Co. KGAA, DE, vol. 265, No. 1-5, Jan. 1, 1927, pp. 15-26.
Hata et al., "Nucleophilic Attack of Intramolecular Hydroxyl Groups on Electron-Rich Aromatics Using Hypervalent Iodine(III) Oxidation", Tetrahedron, Elsevier Science Publishers, Amsterdam, NL, vol. 63, No. 19, Apr. 5, 2007, pp. 4052-4060.

(Continued)

*Primary Examiner* — Nannette Holloman
(74) *Attorney, Agent, or Firm* — Polsinelli PC

(57) ABSTRACT

The present invention relates to the use as a preserving agent, in particular in cosmetic or dermatological composition, of at least one compound of formula (I): in which:—X represents =O or —OH;—R1 represents a hydrogen atom or a methyl;—R2 represents a hydrogen atom, a methyl or an ethyl;—R3 represents a C1-C12, saturated or unsaturated, linear hydrocarbon-based radical, optionally substituted with a hydroxyl group (OH); with the exclusion of the compound of formula (I) in which X represents =O, R1=methyl, R2=H and R3=—(CH$_2$)$_6$—CH$_3$. The invention also relates to certain novel compounds and to the cosmetic or dermatological compositions comprising same.

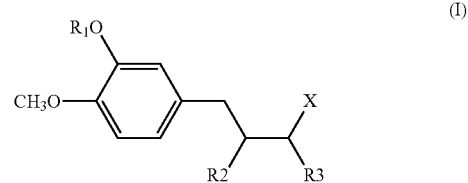

17 Claims, No Drawings

(56) References Cited

OTHER PUBLICATIONS

Seto et al., "Synthesis of 3-hydrosy-4-methoxyphenethyl methyl and ethyl ketones", Science Reports Tohoku Universitat, vol. 33, Jan. 1, 1949, pp. 111-114.

Ahmed M. Galal, "Antimicrobial Activity of 6-Paradol and Related Compounds", International Journal of Pharmacognosy, 1996, vol. 34, No. 1, pp. 64-69.

Chinese Office Action issued Aug. 26, 2015 in Chinese Application No. 20110048775.0 with English translation.

* cited by examiner

USE OF SUBSTITUTED METHOXYALKOXYPHENYLALKYL DERIVATIVES AS PRESERVATIVE, PRESERVING METHOD, COMPOUNDS AND COMPOSITION

CROSS REFERENCE TO RELATED APPLICATIONS

This application is a National Phase filing under 35 U.S.C. §371 of PCT/EP2011/067450 filed on Oct. 6, 2011; and this application claims priority to Application No. 1058182 filed in France on Oct. 8, 2010, and U.S. Provisional Application No. 61/392,082 filed on Oct. 12, 2010 under 35 U.S.C. §119; the entire contents of all are hereby incorporated by reference.

The present invention relates to the use of substituted derivatives of methoxyalkoxyphenylalkyl type, in particular as a preservative in cosmetic or dermatological compositions; the invention also relates to novel compounds that can be used in cosmetology or in dermatology, and also to the compositions comprising these compounds.

It is common practice to introduce chemical preservatives into cosmetic or dermatological compositions, these preservatives being intended to combat the growth of microorganisms in these compositions, which would quickly make them unsuitable for use. It is in particular necessary to protect compositions against microorganisms capable of growing inside the composition, for example during production thereof, and also against those which the user might introduce therein while handling it, in particular when taking up the products in jars with the fingers. Chemical preservatives commonly used are in particular parabens, organic acids or formol-releasing compounds. However, these preservatives have the drawback of causing irritation, in particular on sensitive skin, when they are present at relatively high levels. Moreover, in the interests of the environment, consumers are increasingly searching for environmentally friendly, in particular nonecotoxic, preserving agents. In addition, the effectiveness of the preservatives conventionally used is variable and their formulation can pose problems, in particular of incompatibility, or even of destabilization, of formulas, in particular of emulsions.

One object of the present invention is to propose novel preserving agents which in particular have a broad antimicrobial spectrum, at least as broad, or even broader, than that of the already existing compounds, and which do not have the drawbacks of the prior art, in particular which have specific physicochemical properties making it possible to protect cosmetic formulas against microbial contamination while at the same time being well tolerated.

A subject of the invention is therefore the use as a preserving agent, in particular in a cosmetic or dermatological composition, of at least one compound of formula (I), alone or as a mixture, as defined hereinafter.

The term "preserving agent" is intended to mean a substance which is commonly added to a composition in order to preserve said composition with respect to a contaminating agent. Advantageously, the compounds of formula (I) according to the invention are used as an antimicrobial and/or antibacterial and/or antifungal agent.

Another subject of the invention is a method for preserving a cosmetic or dermatological composition, characterized in that it consists in incorporating into said composition at least one compound of formula (I) as defined hereinafter.

The compounds according to the invention thus correspond to formula (I):

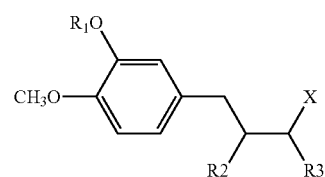

in which:

X represents =O or —OH;

R1 represents a hydrogen atom or a methyl;

R2 represents a hydrogen atom, a methyl or an ethyl;

R3 represents a C1-C12, saturated or unsaturated, linear hydrocarbon-based radical, optionally substituted with a hydroxyl group (OH);

with the exclusion of the compound of formula (I) in which X represents =O, R1=methyl, R2=H and R3=—(CH$_2$)$_6$—CH$_3$.

The term "X represents =O" is intended to mean that C—X represents C=O, C being the carbon atom to which X is attached.

Preferably, R3 is a C1-C6, saturated or unsaturated, linear hydrocarbon-based radical, optionally substituted with a hydroxyl group (OH).

Preferentially, R3 is saturated.

Preferably, R2 represents a hydrogen atom.

Preferably, the compounds of formula (I) are such that:

(i) when R1=H, R3 represents a C1-C12, saturated or unsaturated, linear hydrocarbon-based radical, optionally substituted with a hydroxyl group (OH); preferentially R3 represents a C1-C12, in particular C1-C10, or even C1-C6, even better still C1-C4, saturated linear hydrocarbon-based (alkyl) radical;

(ii) when R1=CH$_3$, R3 represents a C1-C6, saturated or unsaturated, linear hydrocarbon-based radical, optionally substituted with a hydroxyl group (OH); preferentially R3 represents a C1-C6, in particular C1-C5, or even C1-C4, saturated linear hydrocarbon-based (alkyl) radical.

Mention may in particular be made of the following compounds of formula (I):

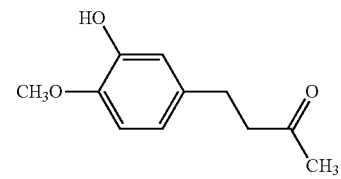

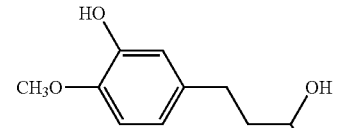

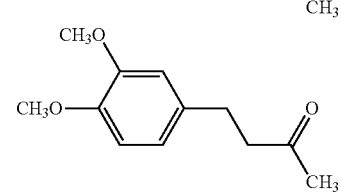

-continued

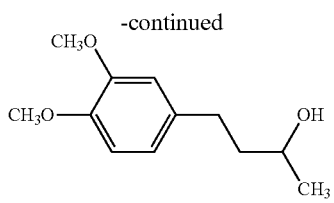

A mixture of compounds of formula (I) can of course be used.

Preferably, the composition does not comprise any preserving agents other than those of formula (I). In particular, the composition preferably does not contain parabens.

Certain compounds of formula (I) are novel and also form a subject of the present invention; they are the compounds of formula (I') hereinafter:

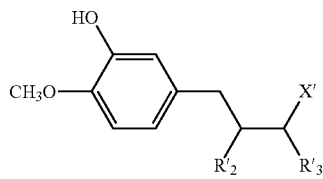

in which:
R'2 represents a hydrogen atom, a methyl or an ethyl;
X' represents =O or —OH,
when X' represents =O, R'3 represents a C3-C12, saturated or unsaturated, linear hydrocarbon-based radical, and
when X' represents OH, R'3 represents a C2-C12, saturated or unsaturated, linear hydrocarbon-based radical.

Preferably, R'3 is a C2-C6, in particular C3-C4, saturated or unsaturated, linear hydrocarbon-based radical. Preferentially, R'3 is saturated (alkyl).

Preferably, R'2 represents a hydrogen atom.

The cosmetic or dermatological compositions comprising at least one compound of formula (I') also form a subject of the present invention.

The compounds of formula (I) can be readily prepared by those skilled in the art on the basis of their general knowledge. They can thus be prepared from commercially available isovanillin (CAS 6221-59-0) when R1=H or from commercially available veratraldehyde (CAS 120-14-9) when R1=methyl, in the following way:

The compounds of formula (I), alone or as a mixture, can be used in a proportion of from 0.01 to 10% by weight, in particular 0.1 to 5% by weight, relative to the weight of the composition, in particular cosmetic or dermatological composition.

The cosmetic or dermatological compositions comprise, moreover, a cosmetically or dermatologically acceptable medium, i.e. a medium which is compatible with keratin materials such as facial or body skin, the lips, the hair, the eyelashes, the eyebrows and the nails.

The compositions according to the invention may be in any of the galenical forms conventionally used, in particular for topical application, and in particular in the form of aqueous or aqueous-alcoholic solutions, of oil-in-water (O/W) or water-in-oil (W/O) or multiple (triple: W/O/W or O/W/O) emulsions, of aqueous gels, or of dispersions of a fatty phase in an aqueous phase by means of spherules, it being possible for these spherules to be polymeric nanoparticles such as nanospheres and nanocapsules, or lipid vesicles of ionic and/or nonionic type (liposomes, niosomes, oleosomes), of nanoemulsions, or of thin films. These compositions are prepared according to the usual methods.

The compositions according to the invention may be more or less fluid and may have the appearance of a white or coloured cream, an ointment, a milk, a lotion, a serum, a paste or a foam. They can optionally be applied to the skin in the form of an aerosol. They can also be in solid form, for example in the form of a stick.

The cosmetic or dermatological composition according to the invention may in particular be in the form:
of a care or makeup product, in particular for facial or body skin, the lips, the eyelashes, the nails, the hair;
of an aftershave gel or lotion;
of a hair-removing cream;
of a suntan or self-tanning composition;
of a body or hair hygiene composition, such as a shower gel or a shampoo;
of a solid cosmetic composition such as a cleansing bar or soap;
of an aerosol composition also comprising a pressurised propellant;
of a hair composition, in particular a hair setting lotion, a styling cream or gel, a dyeing composition, a hair restructuring lotion, a permanent-wave composition, an anti-hair loss lotion or gel;
of a composition for oro-dental use.

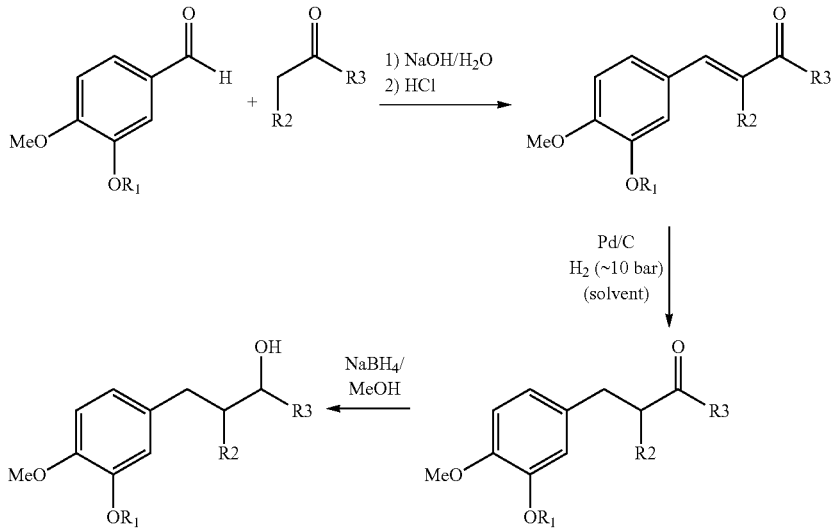

The physiologically acceptable medium in which the compounds can be used, and also its constituents, their amount, the galenical form of the composition and the method for preparing said composition can be chosen by those skilled in the art on the basis of their general knowledge according to the type of composition desired.

In particular, the composition may comprise any fatty substance normally used in the field of application envisaged.

The composition may also comprise an aqueous medium which comprises water, an aqueous-alcoholic medium containing at least one C2-C6 alcohol such as ethanol or isopropanol, or an organic medium comprising customary organic solvents, such as C2-C6 alcohols, in particular ethanol and isopropanol, glycols such as propylene glycol, or ketones.

The composition according to the invention may also comprise the adjuvants customary in the cosmetic and dermatological fields, such as thickeners, emulsifiers, surfactants, gelling agents, active cosmetic agents, fragrances, fillers, colorants, moisturizers, vitamins or polymers. The amounts of these various adjuvants are those conventionally used in the fields under consideration, for example from 0.001 to 20% of the total weight of the composition. These adjuvants, and also their concentrations, should be such that they are not detrimental to the advantageous properties of the compounds according to the invention.

The pH of the compositions according to the invention, when they comprise at least one aqueous phase (aqueous solutions, emulsions for example), is preferably between 4 and 9, preferably between 4 and 7, and advantageously between 5 and 6.

The invention is illustrated in greater detail in the following exemplary embodiments.

EXAMPLE 1

Determination of the Antimicrobial Activity of a Compound According to the Invention The antimicrobial efficacy of a compound of formula (I) was evaluated by the Challenge Test or artificial contamination method.

Compound Tested

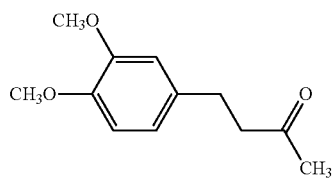

Protocol

The challenge test method consists of an artificial contamination of the sample with microbial strains from collection (bacteria, yeasts and moulds) and of an evaluation of the number of revivable microorganisms seven days after inoculation.

In order to demonstrate the effect of compounds of formula (I), the antimicrobial activity of a cosmetic formula containing 2% of compound according to the invention was compared with the same formula alone (control), after inoculation of approximately $10^6$ CFU (colony-forming units)/gram of cosmetic formula.

Cosmetic Formula (% by Weight)

| | |
|---|---|
| sorbitan tristearate (Span 65 V ® from Croda) | 0.9% |
| polyethylene glycol stearate (40 EO) (Myrj 52 P ® from Croda) | 2.0% |
| mixture of glyceryl mono-distearate (36/64)/potassium stearate | 3.0% |
| fatty acids of vegetable origin (stearic acid/palmitic acid/myristic acid 53/44/3) | 1.0% |
| cetyl alcohol | 3.8% |
| myristyl myristate | 2.0% |
| cyclopentasiloxane | 5.0% |
| fillers | 0.8% |
| glycerol | 3.0% |
| hydrogenated isoparaffin | 7.2% |
| white petroleum jelly | 4% |
| water | qs 100% |

Microorganism Cultures 5 pure cultures of microorganisms are used.

| MICROORGANISMS | Subculturing medium | T° | ATCC |
|---|---|---|---|
| *Escherichia coli* (Ec) | Trypto-casein soy | 35° C. | 8739 |
| *Enterococcus faecalis* (Ef) | Trypto-casein soy | 35° C. | 33186 |
| *Pseudomonas aeruginosa* (Pa) | Trypto-casein soy | 35° C. | 19429 |
| *Candida albicans* (Ca) | Sabouraud | 35° C. | 10231 |
| *Aspergillus niger* (An) | Malt | 35° C. | 6275 |

ATCC = American Type Culture Collection

The gram−bacterial strains (*Escherichia coli* and *Pseudomonas aeruginosa*), the gram+bacterial strain (*Enterococcus faecalis*), the yeast strain (*Candida albicans*), and the mould strain (*Aspergillus niger*) are inoculated into subculturing medium, respectively the day before inoculation for the bacteria and the yeast, and 5 days before inoculation for the mould.

On the day of inoculation:

a suspension in tryptone salt diluent is prepared respectively for the bacteria and the yeast in such a way as to obtain, on a spectrophotometer, a suspension having an optical density between 35% and 45% of transmitted light at 544 nm;

for the mould, the spores are taken by washing the agar with 6 to 7 ml of harvesting solution and the suspension is recovered in a sterile flask or tube.

After having homogenized the microbial suspension, 0.2 ml of inoculum (the suspensions are used pure: between $1 \times 10^8$ and $3 \times 10^8$ CFU per ml) are placed in each pill bottle and the microbial suspension is completely homogenized in the 20 g of product (=cosmetic formula) using a spatula.

The amount of microorganisms present in the product corresponds, after homogenization, to a concentration of $10^6$ microorganisms per gram of product, i.e. the inoculation at 1% of an inoculum containing $10^8$ microorganisms per ml. After 7 or 14 days of contact time between the microorganisms and the product at 22° C.±2° C. and in the dark, ten-fold dilutions are carried out and the number of revivable microorganisms remaining in the product is counted.

Results

| | Amount | Number of CFU/gram of product at T = 7 days ||||||
| | | E. coli | P. aeruginosa | E. faecalis | C. albicans | A. niger |
|---|---|---|---|---|---|---|
| Compound | 2% | <200 | <200 | $7.3 \cdot 10^5$ | <200 | $1.4 \cdot 10^6$ |

<200 CFU: sensitivity threshold of the method

| | Amount | Number of CFU/gram of product at T = 14 days |||||
| | | E. coli | P. aeruginosa | E. faecalis | C. albicans | A. niger |
|---|---|---|---|---|---|---|
| Compound | 2% | — | — | $3.3 \cdot 10^8$ | — | $3.6 \cdot 10^5$ |

<200 CFU: sensitivity threshold of the method

The invention claimed is:

1. A method for preserving a cosmetic or dermatological composition, which comprises incorporating into said composition at least one compound of formula (I), alone or as a mixture:

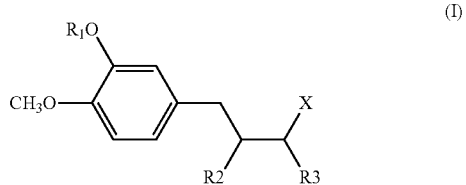

in which:
X represents =O or —OH;
$R_1$ represents a hydrogen atom or a methyl;
R2 represents a hydrogen atom, a methyl or an ethyl;
R3 represents a C1-C12, saturated or unsaturated, linear hydrocarbon-based radical, optionally substituted with a hydroxyl group (OH);
with the exclusion of the compound of formula (I) in which X represents =O, R1=methyl, R2=H and R3=—(CH$_2$)$_6$—CH$_3$, wherein the compound of formula (I), alone or as a mixture, is present in a proportion of from 0.01 to 10% by weight.

2. The method according to claim 1, in which the compounds correspond to formula (I), in which:
R3 is a C1-C6, saturated or unsaturated, linear hydrocarbon-based radical, optionally substituted with a hydroxyl group (OH) and/or
R2 represents a hydrogen atom.

3. The method according to claim 1, in which R3 is saturated.

4. The method according to claim 1, in which the compounds of formula (I) are chosen from the following compounds:

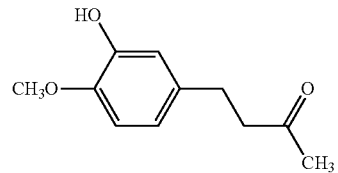

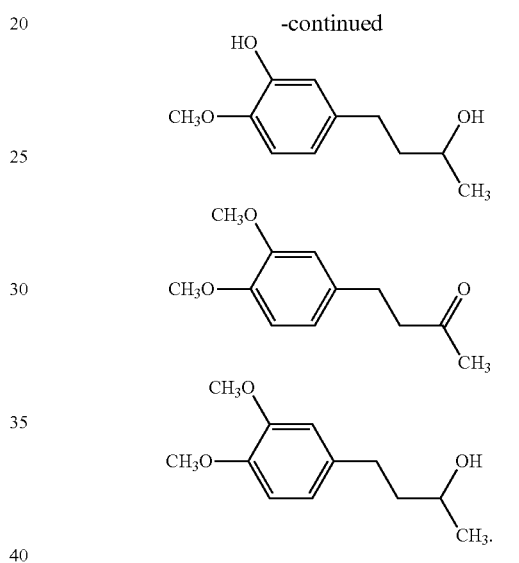

5. The method according to claim 1, in which the compound of formula (I), alone or as a mixture, is present in a proportion of 0.1 to 5% by weight, relative to the weight of the composition.

6. The method according to claim 1, in which the composition comprises a physiologically acceptable medium which comprises at least one ingredient chosen from fatty substances; water; C2-C6 alcohols; glycols, ketones; thickeners, emulsifiers, surfactants, gelling agents, active cosmetic agents, fragrances, fillers, colorants, moisturizers, vitamins and polymers.

7. The method according to claim 4, in which the compound of formula (I), alone or as a mixture, is present in a proportion of from 0.1 to 5% by weight relative to the weight of the composition.

8. The method according to claim 7, in which the composition is in the form of a care or makeup product; of an aftershave gel or lotion; of a hair-removing cream; of a suntan or self-tanning composition; of a body or hair hygiene composition; of a dermatological composition; of a solid cosmetic composition; of an aerosol composition; of a hair composition; or of a composition for oro-dental use.

9. The method according to claim 1, in which the composition is in the form of a care or makeup product; of an aftershave gel or lotion; of a hair-removing cream; of a suntan or self-tanning composition; of a body or hair hygiene composition; of a dermatological composition; of a solid cosmetic composition; of an aerosol composition; of a hair composition; or of a composition for oro-dental use.

10. The method according to claim 2, in which R3 is saturated.

11. The method according to claim 5, in which the compounds of formula (I) are chosen from the following compounds:

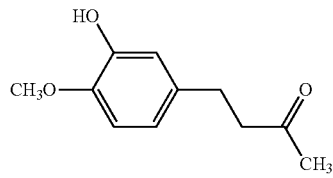
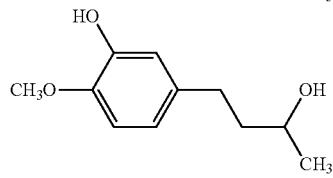
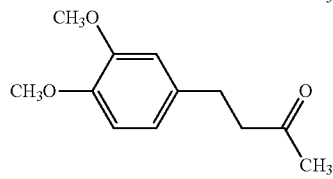
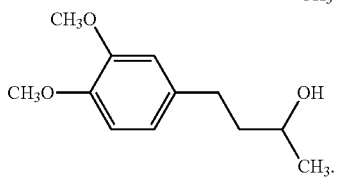

12. The method according to claim 6, in which the compounds of formula (I) are chosen from the following compounds:

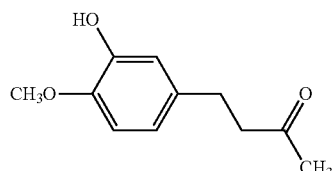
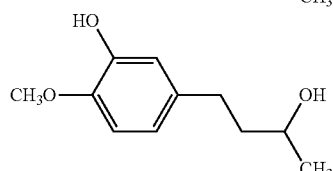
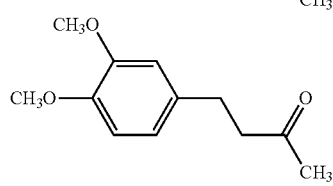

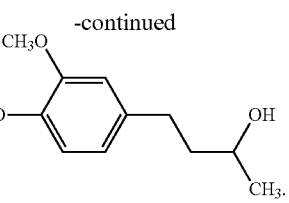

13. The method according to claim 2, in which the compound of formula (I), alone or as a mixture, is present in a proportion of from 0.1 to 5% by weight relative to the weight of the composition.

14. The method according to claim 3, in which the compound of formula (I), alone or as a mixture, is present in a proportion of from 0.1 to 5% by weight relative to the weight of the composition.

15. The method according to claim 1, in which the compound of formula (I) is selected from the group consisting:

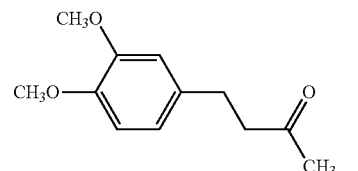
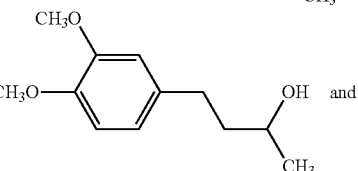
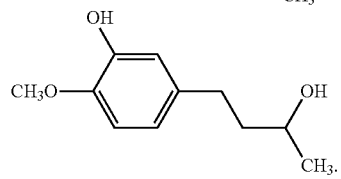

16. The method according to claim 1, in which the compound of formula (I) is

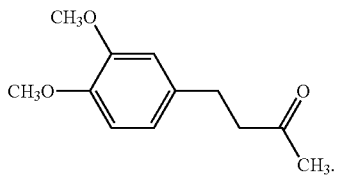

17. The method according to claim 1, wherein R3 is a C1-C4 alkyl radical.

* * * * *